(12) United States Patent
Bommer et al.

(10) Patent No.: US 7,830,523 B2
(45) Date of Patent: Nov. 9, 2010

(54) NONDESTRUCTIVE INSPECTION OF A STRUCTURE INCLUDING THE ANALYSIS OF CAVITY ELECTROMAGNETIC FIELD RESPONSE

(75) Inventors: Jason Philip Bommer, Tacoma, WA (US); William John Whetham, Seattle, WA (US)

(73) Assignee: The Boeing Company, Chicago, IL (US)

( * ) Notice: Subject to any disclaimer, the term of this patent is extended or adjusted under 35 U.S.C. 154(b) by 412 days.

(21) Appl. No.: 11/925,622

(22) Filed: Oct. 26, 2007

(65) Prior Publication Data

US 2009/0108211 A1   Apr. 30, 2009

(51) Int. Cl.
*G01B 9/02* (2006.01)
(52) U.S. Cl. .................................................. 356/450
(58) Field of Classification Search .................. 356/450; 73/634
See application file for complete search history.

(56) References Cited

U.S. PATENT DOCUMENTS

| | | | |
|---|---|---|---|
| 2,491,418 A | 12/1949 | Schlesman | |
| 2,630,472 A | 3/1953 | McArthur | |
| 5,170,666 A | 12/1992 | Larsen | |
| 7,205,956 B1 | 4/2007 | Sychaleum et al. | |
| 7,277,822 B2 | 10/2007 | Blemel | |
| 2007/0046298 A1 | 3/2007 | Safai et al. | |
| 2007/0090294 A1 | 4/2007 | Safai et al. | |
| 2007/0151375 A1 | 7/2007 | Kennedy et al. | |

FOREIGN PATENT DOCUMENTS

| | | |
|---|---|---|
| JP | 2005 291708 | 10/2005 |
| WO | 2004102056 A2 | 11/2004 |

OTHER PUBLICATIONS

Shibata et al., "Experimental study on NDT method using electromagnetic waves," Journal of Materials Processing Technology, vol. 161, No. 1-2, Apr. 10, 2005, pp. 348-352.
Abbasi et al., "Microwave Nondestructive Detection of Longitudinal Cracks in Pipe with U-bend and Prediction of its Location by Signal Processing" Electromagnetic Nondestructive Evaluation (XI), A Tamburrino et al. (Eds), vol. 31, Oct. 2008, pp. 154-161.
Caspers et al., "Waveguide mode reflectometry for obstacle detection in the LHC beam pipe including signal attenuation" Proceedings of the 2003 Particle Accelerator Conference. PAC 2003. Portland, OR, May 12-16, 2003; [Particle Accelerator Conference], New York, NY :IEEE, US, vol. 4, May 12, 2003, pp. 2700-2702.
Hldaio et al., "A passive wireless displacement sensor for structural health monitoring of civil structures" Proceedings of SPIE—The International Society for Optical Engineering -Nondestructive Characterization for Composite Materials, Aerospace Engineering, Civil Infrastructure, and Homeland Security 2007 SPIE US, vol. 6531, Apr. 19, 2007.
"Aperture Excitation of Electrically Large, Lossy Cavities", Hill, D.A; Ma M.T..; Ondrejka A.R.; Riddle B.F.; Crawford M. L.; Johnk R.T , IEEE Trans. On Electromagnetic Compatibility, vol. 36, No. 3, Aug. 1994.

*Primary Examiner*—Michael A Lyons

(57) ABSTRACT

Nondestructive inspection (NDI) on a structure having a cavity includes exciting the structure with electromagnetic radiation and analyzing the cavity's electromagnetic field response to detect a state change of the structure.

28 Claims, 4 Drawing Sheets

EXCITE A STRUCTURE HAVING A CAVITY WITH ELECTROMAGNETIC RADIATION — 110

ANALYZE THE CAVITY'S ELECTROMAGNETIC FIELD RESPONSE TO DETECT A STATE CHANGE OF THE STRUCTURE — 120

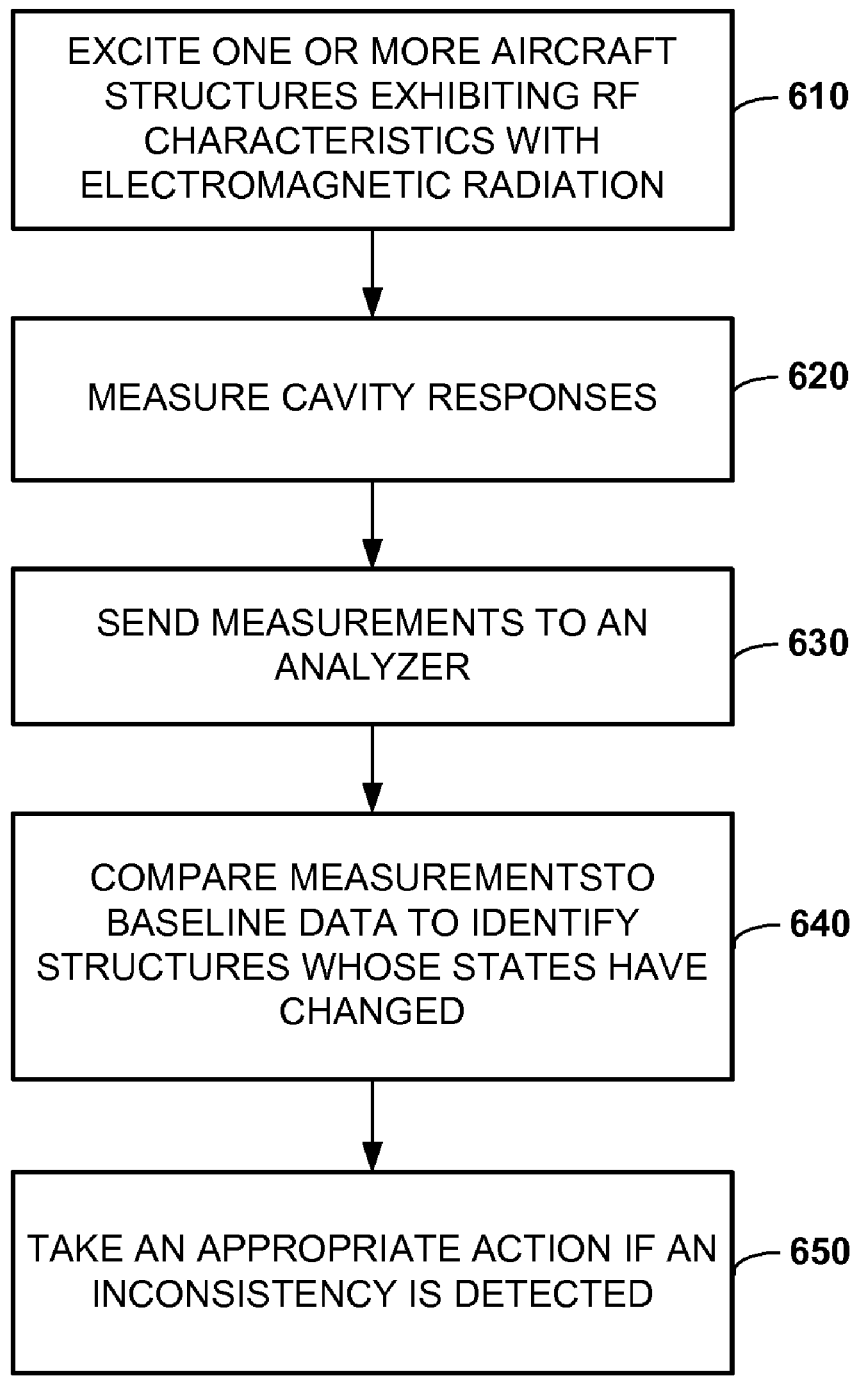

NONDESTRUCTIVE INSPECTION OF A STRUCTURE INCLUDING THE ANALYSIS OF CAVITY ELECTROMAGNETIC FIELD RESPONSE

BACKGROUND

Nondestructive inspection (NDI) of a structure involves thoroughly examining the structure without harming it or significantly disassembling it. Nondestructive inspection is commonly used in the aircraft industry to validate the health (e.g., integrity and fitness) of aircraft structures.

Manual NDI of aircraft structures is time consuming and labor intensive. Semi-automatic and fully automatic NDI are less labor intensive and provide better quality and process control than manual NDI.

SUMMARY

According to an aspect of the present invention, NDI is performed on a structure having a cavity. The NDI includes exciting the structure with electromagnetic radiation and analyzing the cavity's electromagnetic field response to detect a state change of the structure.

BRIEF DESCRIPTION OF THE DRAWINGS

FIG. 6 is an illustration of a method for assessing structural health of an aircraft in accordance with an embodiment of the present invention.

DETAILED DESCRIPTION

Figure 1:
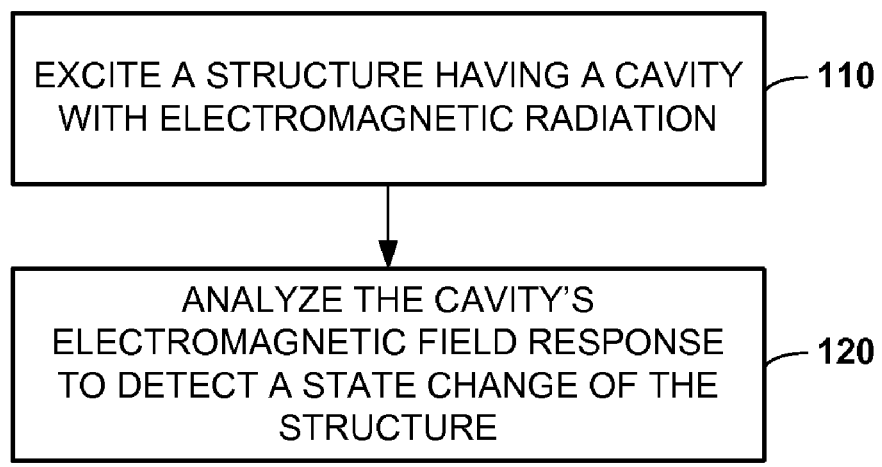
FIG. 1 is an illustration of a method in accordance with an embodiment of the present invention.

Reference is made to FIG. 1, which illustrates a method of performing NDI on a structure. The structure has a cavity. The cavity may be completed bounded by the structure, or the cavity may be substantially bounded by structure (e.g., the structure may have holes, apertures, or other opening to the cavity).

The structure having the cavity exhibits RF characteristics. When excited with electromagnetic radiation, the structure interacts with the electromagnetic radiation, causing a distinct electromagnetic field response. This cavity response includes reflected, absorbed, and transmitted components of the electromagnetic radiation. The RF characteristics are structure-specific (e.g., a function of geometry, surface conductivity, etc.).

The structure is not limited to any particular geometry or composition. The composition could include a metal (e.g., aluminum, titanium, alloys thereof), composite material (e.g., carbon fiber reinforced plastic), etc.

At block 110, the structure is excited with electromagnetic radiation (this electromagnetic radiation will also be referred to as the "excitation"). The cavity may exhibit characteristics of fundamental mode waveguide propagation as well as higher-order resonant cavity modes. The electromagnetic radiation may be propagated from end-to-end of the structure as in an electromagnetic waveguide, or it may introduce a standing wave, such as with a cavity resonator The electromagnetic radiation may be generated by a radiating element. The radiating element is not limited to anything in particular. In some embodiments, the radiating element may be a discrete transmit antenna. In other embodiments, the radiating element may be the structure itself (e.g., a current is run through the structure). In some embodiments, a simple aperture may be used to introduce the excitation. For instance, electromagnetic radiation could be piped in from a vent into an isolated cavity. In some embodiments, a slot antenna may be used to introduce the excitation. With a slot antenna, surface current would be driven on the outside or inside of a cavity wall and the slot would resonate and radiate energy into the cavity.

In some embodiments, the excitation may have a dominant magnetic field component. In other embodiments, the excitation may have a dominant electric field component.

In some embodiments, the radiating element may be temporarily attached to the structure. If temporarily attached, the radiating element can be removed and used in another location.

At block 120, the cavity's electromagnetic field response is analyzed to detect state changes of the structure. Certain state changes can cause a noticeable change in the field distribution throughout the cavity. That is, an electromagnetic field distribution corresponding to a healthy structure will be noticeably different than an electromagnetic field distribution corresponding to a structure whose state has changed. Such state changes include, without limitation, cracks, corrosion, changes in geometry (e.g., expansion, contraction, contortion), delamination, disbanding, buckling, fiber break-out, penetration, fluid ingress (e.g., water, fuel), etc. Thus, by analyzing the cavity response to the excitation, certain types of state changes of the structure can be revealed.

The frequency content of the excitation will be a function of cavity geometry, as well as locations of elements (e.g., antennas) that radiate the excitation and measure the cavity response in order to properly exploit the resonant characteristics of the cavity. In some embodiments, the frequency could be in the megahertz or gigahertz range.

Figure 2:
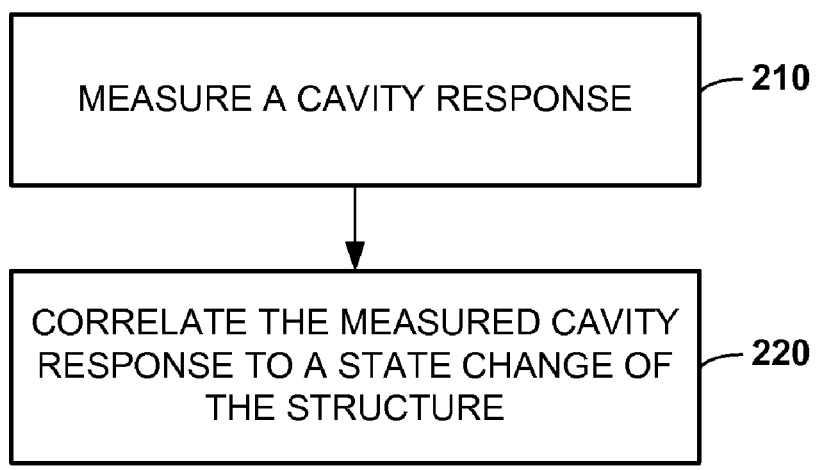
FIG. 2 is an illustration of a method of analyzing a cavity response in accordance with an embodiment of the present invention.

Reference is now made to FIG. 2, which illustrates an exemplary method of analyzing a cavity response. At block 210, the cavity response is measured. For instance, the cavity response is received by a receive antenna, and the received signal is sampled.

At block 220, the measured cavity response is correlated to a state change of the structure. This may be done by comparing the measurements to baseline data, where the baseline data corresponds to different cavity responses of a structure.

Figure 3:
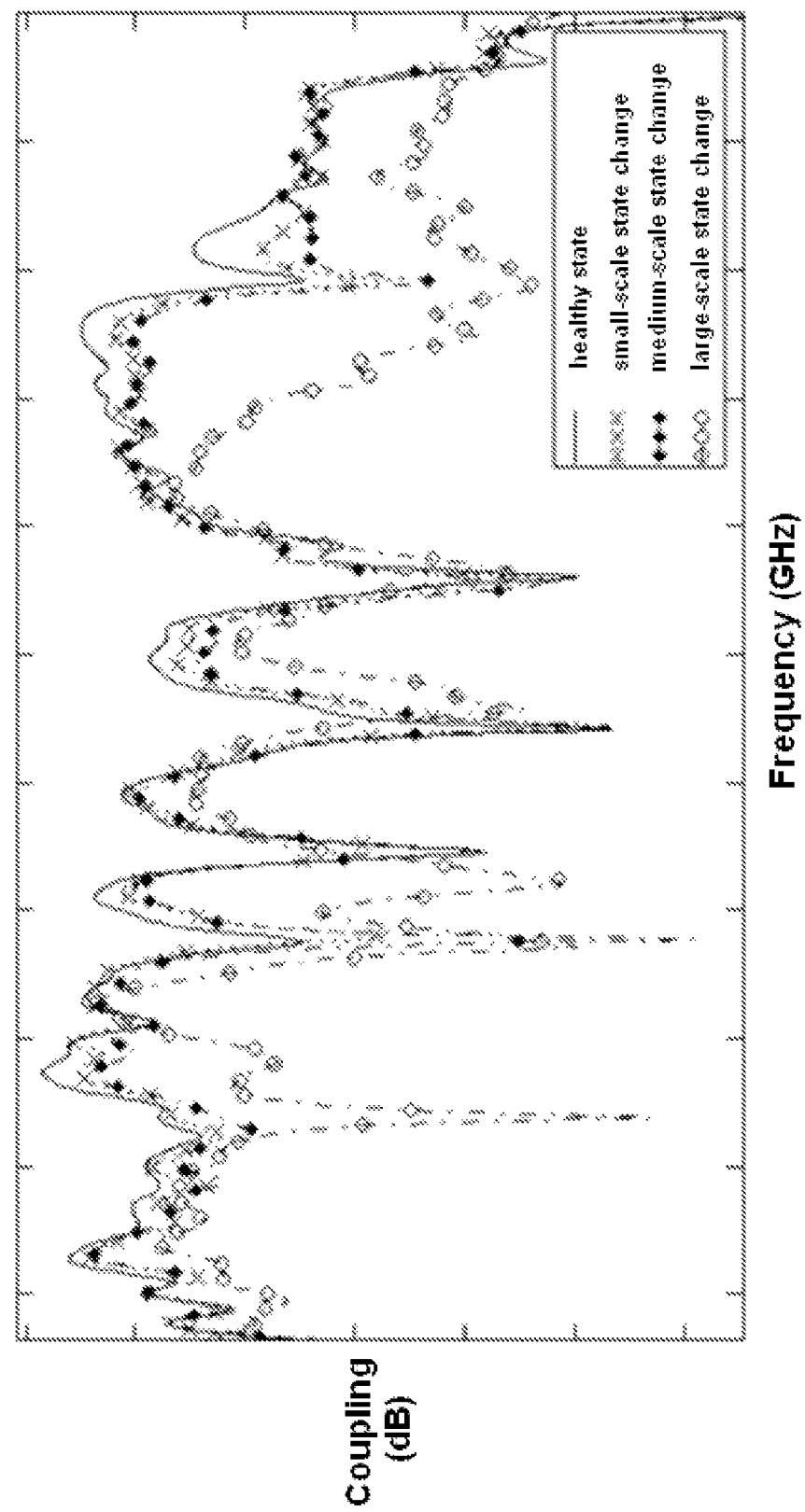
FIG. 3 is an illustration of exemplary baseline data corresponding to a structure with and without certain state changes.

FIG. 3 is an illustration of experimental baseline data on a composite tube of the type used as a fuselage stiffener. The baseline data includes different curves of coupling (a ratio of receive power to transmit power) versus frequency for the structure. A curve represented by a solid line corresponds to a healthy tube having closed ends. The tube was excited at one end, and the cavity response was measured at the opposite end. Excitation was performed at different frequencies. The tube exhibited the characteristics of an electromagnetic waveguide. At the higher excitation frequencies, the tube also exhibited the characteristics of a cavity resonator.

Three other curves correspond to the tube with different state changes. Of these three curves, a curve represented by crosses (x x x) corresponds to the structure with small crack (a small-scale state change), a curve represented by diamonds (♦ ♦ ♦) corresponds to the structure with a larger crack (a medium-scale state change), and a curve represented by circles (○ ○ ○) represents the structure with an open end (a large-scale state change).

The difference between the curve indicating a healthy structure and any of the other curves is noticeable. Yet not only do those other curves identify an unhealthy structure, they can also identify the nature and degree of a state change. The nature of a state change can be identified because the curves can correspond to a particular type of state change (e.g., a crack). The degree of a state change can be identified because the curves can correspond to state changes of different sizes or locations. For instance, field responses can be measured for a structure having cracks of different sizes or cracks in different locations.

NDI according to an embodiment of the present invention can be applied to a system having multiple structures and cavities. Exemplary systems include aircraft, ships and submarines, rockets, automobiles, trains, and other vehicles. Other exemplary systems include, without limitation, cargo containers, satellites, buildings, and bridges.

However, the NDI is particularly advantageous for aircraft. Inspection of an aircraft can be fully automated, and it can be performed quickly and inexpensively. A quick diagnosis can be made without any advance knowledge of the location of a state change.

Moreover, the NDI can be performed in-flight. One advantage of in-flight NDI is that the health of an aircraft can be assessed after a lightning strike. Another advantage is that the health of an aircraft can be assessed during and after severe turbulence.

Figure 4:
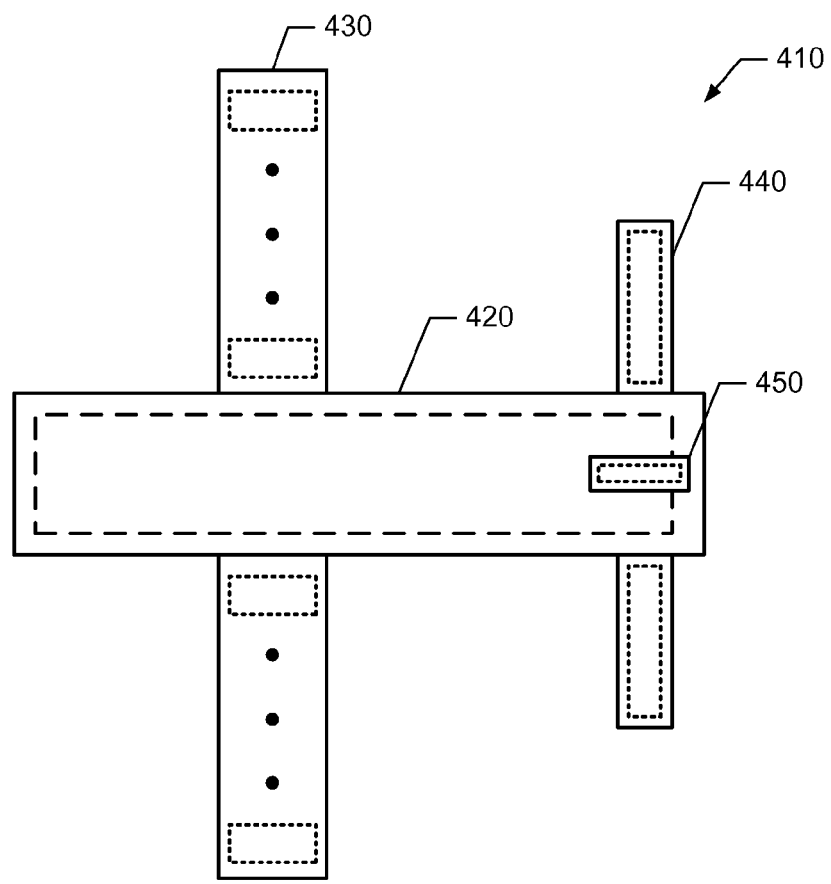
FIG. 4 is an illustration of an aircraft.
Figure 5:
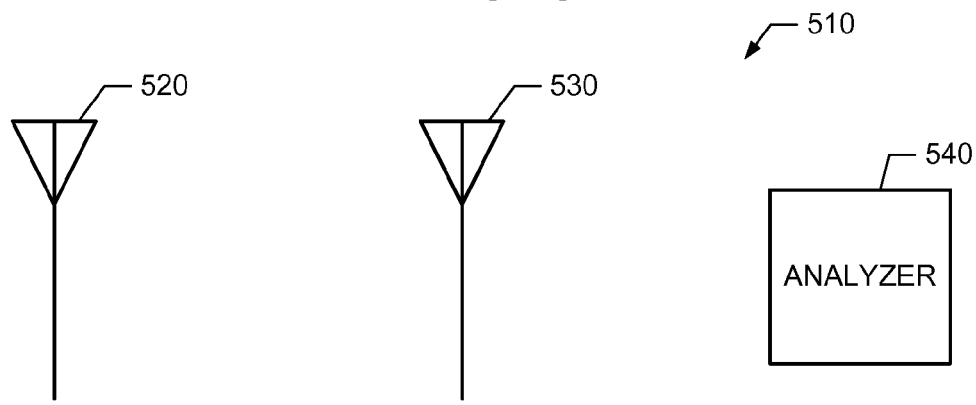
FIG. 5 is an illustration of apparatus for assessing structural health in accordance with an embodiment of the present invention.

FIGS. 4 and 5 illustrate an aircraft 410 and apparatus 510 that may be used to analyze the structural health of the aircraft 410. Referring to FIG. 4, the aircraft 410 includes a plurality of structures 420-450 (indicated by solid lines) having cavities (indicated by dashed lines). Exemplary structures include, but are not limited to, a fuselage 420, wings 430, wheel wells, leading and trailing edges of the wing, air ducts, horizontal and vertical stabilizers 440 and 450, fairings, radomes, floor beams, cargo holds, ducting, etc.

A fuselage 420 may be treated as a structure having a single cavity. A wing may 430 be treated as a structure having one or more cavities. The wing 430 includes front and rear spars, ribs there between, and upper and lower surface panels. The wing 430 may be treated as a structure having a single cavity bounded by the spars and surface panels, or it may be treated as a structure having multiple cavities, where each cavity is bounded by ribs and portions of the spars and panels. Other cavities include areas within the leading and trailing edges, engine mount pylons, and fairings. Still other cavities may be present in structures such as tubes, vents and ducts (e.g., a large fuel tube or an environmental control system duct). These cavities are considered "natural" cavities of the aircraft.

The aircraft 410 has other cavities as well. These other cavities (not shown) include, but are not limited to, spaces under galleys and lavatories, engine cowlings, and flap track fairings.

Cavities can change form during flight. As a first example, when the airplane is in normal flight and its flaps are up, a cavity will likely be along the wing/flap interface. As the flaps start to extend, the cavity will change. Eventually the interface may no longer appear as a cavity when the flaps are fully deployed. As a second example, on the bottom of a wing are fairings that house flight control jack screws. Various states of flight can probably be characterized inside these little cavities as the internal mechanisms change forms.

Many, if not all, of these cavities are formed by structures exhibiting RF characteristics. However, the aircraft 410 might also include structures that do not exhibit RF characteristics.

Additional reference is now made to FIG. 5. In some embodiments, the aircraft 410 may include one or more radiating structures 520 for providing electromagnetic excitation (the radiating structures are represented schematically by a single transmit antenna 520). In some embodiments, a radiating structure 520 can be a transmit antenna, which can be located inside or outside of a cavity. In the alternative, one or more of the aircraft structures can be used to provide excitation. That is, those aircraft structures can function as radiating structures 520.

The aircraft 410 includes one or more receive antennas 530 for measuring the cavity response to the electromagnetic excitation (this is represented schematically by the single receive antenna 530). The measurements contain information about any state changes of the structures. One or more receive antennas may be provided for each structure. The receive antennae may be located inside or outside the structures' cavities.

The radiating elements and receive antennas 520 and 530 may be low profile passive antennas that are integrated with the aircraft 410. For instance, a circuit board with an engraved antenna could be secured to an aircraft structure or integrated directly into the structural design. Certain cavities might use multiple radiating elements 520 and receivers 530 to properly characterize a healthy structure.

An analyzer 540 analyzes the measurements of the cavity responses to detect any state changes of the aircraft structures. The analyzer 540 may include a computer that is programmed with software for analyzing the measurements. The analyzer 540 could be on board the aircraft (e.g., as a standalone computer or integrated with an on-board computer), or it could be a ground-based system (e.g., as a standalone computer or integrated with another ground-based system).

The analyzer 540 or a separate circuit may generate the excitation and supply the excitation to the radiating elements 520. Continuous wave illumination (narrow band frequency) or pulsed illumination (broad band) may be used to create the excitation.

Reference is now made to FIG. 6, which illustrates a method for assessing the structural health of an aircraft. At block 610, one or more structures having cavities and exhibiting RF characteristics are excited with electromagnetic radiation.

At block 620, the cavity responses to the excitations are measured. The measurements provide information about any state changes of the structures.

At block 630, the measurements are sent to an analyzer. The measurements may be sent to an analyzer that is on-board the aircraft, and/or it may be transmitted to an analyzer that is on the ground.

At block 640, the measurements are compared to baseline data to identify any structures having state changes. The baseline data may take flight conditions into account, since different flight conditions can have different effects on the cavity responses. For instance, a wing cavity will produce a slightly different response on the ground than it will in the air due to the contorting and twisting. The baseline data can be easily calibrated. Each cavity response can be measured when the aircraft is new (on the ground and in-flight), or under controlled conditions.

Variations in a structure due to temperature, ambient pressure, or system vibration can also be sensed. The changes in the measurements due to these variations can be identified and accounted for. Nominal noise variations can also be filtered out.

Other types of measurements can be used to determine whether any of the structures have state changes and also to provide a more comprehensive understanding of the states of the structures. Sensors such as thermal, vibration and strain sensors may provide these other types of measurements.

At block 650, if a state change is detected, an appropriate action is taken. As a first example, a pilot is notified that the structural health of the aircraft is in question. The pilot might also be notified as to the structures whose states have changed, as well as the nature and degree of the state changes. A recommendation can then be made as to aborting or continuing the flight. As a second example, if the analysis reveals a state change, additional NDI could be performed by the ground crew after the plane has landed, or it could be performed later by a vehicle health maintenance service (VHMS). Once the aircraft is on the ground, the additional NDI could be performed using conventional techniques. As a third example, no action is taken.

The functions at blocks 610-650 may be performed as part of general health monitoring. The electromagnetic responses can be measured continuously for health checking or at the request of the ground crew or pilot. The NDI can be performed, and the structural health of the aircraft can be assessed, while the aircraft is in-flight.

If the aircraft is struck by lightning or a foreign object (e.g., a bird) during flight, the analysis will immediately and automatically identify any structural members that were affected. If the aircraft undergoes severe electrical or mechanical stress (due, to turbulence, for instance), the analysis will identify any structural members that were affected.

NDI according to the present invention can be fully automated. It is low-cost, light-weight, and low-maintenance.

The in-flight testing increases aircraft safety. NDI according to the present invention can also reduce an airline's maintenance costs and eliminate the need to abort flights for non-critical flight problems.

In general, NDI according to the present invention can be performed on a vehicle (not just an aircraft) while the vehicle is moving. It may also be performed on other structures, such as on buildings after an earthquake, etc.

NDI according to the present invention can be used to detect state changes other than those that relate to structural health (cracks, corrosion, delamination, disbanding, etc.). For instance, NDI according to the present invention may be used to detect a state change such as an improperly sealed door or window. It could also be used to detect improperly closed access panels around a structure.

The invention claimed is:

1. A method comprising performing nondestructive inspection (NDI) on a structure having a cavity, the NDI including exciting the structure with electromagnetic radiation; analyzing the cavity's electromagnetic field response to detect a state change of the structure; and providing an indication of structural health of the structure based on the analysis of the cavity response.

2. The method of claim 1, wherein the structure is excited to exhibit the characteristics of an electromagnetic waveguide.

3. The method of claim 1, wherein the structure is excited to exhibit the characteristics of a cavity resonator.

4. The method of claim 1, wherein the excitation has a dominant electric field component.

5. The method of claim 1, wherein the excitation has a dominant magnetic field component.

6. The method of claim 1, wherein providing the indication includes correlating the cavity response to a state change of the structure.

7. The method of claim 1, wherein detecting the state change includes measuring the cavity response; and wherein providing the indication includes comparing the measurements to baseline data for the structure.

8. The method of claim 1, wherein the NDI is performed continuously and the indication is provided automatically.

9. The method of claim 1, wherein the structure is an aircraft structure; and wherein the NDI is performed in-flight.

10. The method of claim 9, wherein the NDI is performed following a lightning strike.

11. A method of analyzing structural health of an aircraft, the method comprising exciting different aircraft structures exhibiting RF characteristics with electromagnetic radiation and analyzing cavity responses to detect state changes of the structures.

12. The method of claim 11, wherein the excitation and analysis are performed in-flight.

13. The method of claim 11, wherein the excitation and analysis are performed following a lightning strike.

14. The method of claim 11, wherein the excitation and analysis are performed following severe turbulence.

15. The method of claim 11, further comprising identifying those structures whose states changed.

16. The method of claim 11 wherein providing the indication includes identifying the nature and degree of any state changes from signatures and sizes of the responses.

17. The method of claim 11, wherein analyzing the cavity responses includes correlating measurements of the cavity responses to baseline data for the aircraft structures.

18. The method of claim 11, wherein the at least one structure excited with electromagnetic radiation includes at least one of a fuselage, wings and stabilizers.

19. The method of claim 11, wherein the aircraft structures include a fuselage, and wherein the fuselage is excited and analyzed as a single cavity.

20. The method of claim 11, wherein the aircraft structures includes wings, and wherein each wing is excited and analyzed as having multiple cavities.

21. Apparatus comprising an analyzer for performing nondestructive inspection (NDI) on a structure having a cavity, the analyzer analyzing measurements of cavity responses to electromagnetic excitation of the structure, the analysis performed to detect a state change of the structure; the analyzer also providing an indication of structural health of the structure after the cavity response has been analyzed.

22. The apparatus of claim 21, further comprising at least one element for providing the electromagnetic excitation and measuring the cavity responses.

23. An aircraft comprising a plurality of structures having cavities; and a system for performing performing nondestructive inspection (NDI) on at least one of the structures, the system including
electromagnetic excitation apparatus for exciting at least one of those structures exhibiting RF characteristics with electromagnetic radiation; and
field response measurement apparatus for measuring field responses to the electromagnetic excitation, the measurements providing information about any state changes of the structures excited with electromagnetic radiation.

24. The aircraft of claim 23, further comprising an analyzer for analyzing the measurements to detect any state changes of the structures.

25. The aircraft of claim 23, wherein the excitation apparatus and the measurement apparatus are operable during flight.

26. The aircraft of claim 23, wherein the state changes include those state changes that relate to structural health of the aircraft.

27. The aircraft of claim 23, further comprising a system for suggesting an appropriate action in response to those state changes that relate to the structural health of the aircraft.

28. The aircraft of claim 23, wherein the electromagnetic excitation apparatus includes a passive antenna that is integrated with an aircraft structure.

* * * * *